United States Patent
Park et al.

(10) Patent No.: US 10,283,339 B2
(45) Date of Patent: May 7, 2019

(54) PARTICLE BEAM MASS SPECTROMETER AND PARTICLE MEASUREMENT METHOD BY MEANS OF SAME

(71) Applicant: KOREA RESEARCH INSTITUTE OF STANDARDS AND SCIENCE, Daejeon (KR)

(72) Inventors: Chang Joon Park, Sejong (KR); Sang Jung Ahn, Daejeon (KR); Cheolsu Han, Suwon-si (KR); Keu Chan Lee, Daejeon (KR); Seok Rae Yoon, Seoul (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 116 days.

(21) Appl. No.: 15/518,408

(22) PCT Filed: Oct. 7, 2015

(86) PCT No.: PCT/KR2015/010578
§ 371 (c)(1),
(2) Date: Apr. 11, 2017

(87) PCT Pub. No.: WO2016/068507
PCT Pub. Date: May 6, 2016

(65) Prior Publication Data
US 2018/0286655 A1    Oct. 4, 2018

(30) Foreign Application Priority Data
Oct. 29, 2014   (KR) ................. 10-2014-0148024

(51) Int. Cl.
*H01J 49/14*   (2006.01)
*G01N 27/62*   (2006.01)
(Continued)

(52) U.S. Cl.
CPC ............ *H01J 49/147* (2013.01); *G01N 27/62* (2013.01); *H01J 49/0031* (2013.01);
(Continued)

(58) Field of Classification Search
USPC ................. 250/281, 282, 283, 397
See application file for complete search history.

(56) References Cited

U.S. PATENT DOCUMENTS

| 2002/0121599 A1* | 9/2002 | Kato ............... H01J 49/04 250/288 |
| 2006/0113464 A1* | 6/2006 | Litherland ......... B01D 59/44 250/288 |

(Continued)

FOREIGN PATENT DOCUMENTS

| JP | 10-144254 A | 5/1998 |
| JP | 2013101918 A | 5/2013 |

(Continued)

OTHER PUBLICATIONS

Office Action from the Korea Patent Office, dated Mar. 23, 2016.
International Search Report of PCT/KR2015/010578, dated Jan. 14, 2016, English translation.

*Primary Examiner* — Kiet T Nguyen
(74) *Attorney, Agent, or Firm* — STIP Law Group, LLC (57) ABSTRACT

The present invention relates to a particle beam mass spectrometer and particle measurement method by means of same. More particularly, the present invention relates to a particle beam mass spectrometer including: a particle focusing unit focusing a particle beam induced by gas flow; an electron gun forming a charged particle beam by accelerating thermal electrons to ionize the particle beam focused by the particle focusing unit; a deflector deflecting the charged particle beam according to kinetic energy to charge ratio; and a sensing unit measuring a current induced by the deflected charged particle beam, wherein the deflector (Continued)

includes at least one particle beam separation electrode provided at each of opposite sides with respect to a progress axis of the charged particle beam before being deflected.

10 Claims, 8 Drawing Sheets

(51) Int. Cl.
    *H01J 49/26*     (2006.01)
    *H01J 49/00*     (2006.01)
    *H01J 49/06*     (2006.01)
    *H01J 49/42*     (2006.01)

(52) U.S. Cl.
    CPC ............ *H01J 49/061* (2013.01); *H01J 49/26* (2013.01); *H01J 49/4225* (2013.01)

(56) References Cited

U.S. PATENT DOCUMENTS

| | | |
|---|---|---|
| 2008/0001080 A1 | 1/2008 | Suits et al. |
| 2010/0193681 A1 | 8/2010 | Vestal |
| 2014/0151573 A1 | 6/2014 | Wan |

FOREIGN PATENT DOCUMENTS

| | | |
|---|---|---|
| KR | 101104213 A | 4/2011 |
| KR | 1020130116986 A | 10/2013 |

\* cited by examiner

Va: Negative voltage
Vb: Positive voltage

Total Charged Particles
Va=Vb=0

PARTICLE BEAM MASS SPECTROMETER AND PARTICLE MEASUREMENT METHOD BY MEANS OF SAME

CROSS-REFERENCE TO RELATED APPLICATIONS

This application is the U.S. National Phase under 35 U.S.C. § 371 of International Application No. PCT/KR2015/010578 filed on Oct. 7, 2015, which in turn claims the benefit of Korean Application No. 10-2014-0148024, filed on Oct. 29, 2014, the disclosures of which are incorporated by reference into the present application.

TECHNICAL FIELD

The present invention relates to a particle beam mass spectrometer and particle measurement method by means of same.

BACKGROUND ART

Generally, fine particles generated during semiconductor process are a factor that greatly influences manufacturing yield in the semiconductor process where a fine pattern process is required. Most semiconductor processes are performed under lower pressure, and require a particle measurement apparatus operated under low pressure. Particularly, a chemical vapor deposition process has a large part of the semiconductor process. Therefore, in the chemical vapor deposition process, a technology for immediately removing pollutants through real-time monitoring for particle occurrence is necessary to prevent occurrence of defects caused by the fine particles.

In the meantime, a particle beam mass spectrometer is an apparatus for separating gas and particles in an environment where gas and particles are mixed, and for measuring the size of ultra-fine particles by using an electrical filter after ionizing the particles separated from the gas.

In a working environment of the semiconductor process, etc. performed in a vacuum state under low pressure, gas and ultra-fine particles are mixed, and in this case, a particle beam mass spectrometer may be used as an apparatus for monitoring the particle content in real-time.

In regard to manufacturing a particle beam mass spectrometer, Korean patent No. 10-1104213 (9 Jan. 2012) disclosed a particle beam mass spectrometer operated by using an electron gun having high efficiency without loss of thermal electrons in a low-pressure region, and the particle beam mass spectrometer can reduce the use pressure of the particle beam mass spectrometer by using a high efficiency electron gun, thereby reducing manufacturing costs of the apparatus. In addition, Korean patent No. 10-1360891 (12 Feb. 2014) disclosed an apparatus for simultaneously realizing both a function of a conventional particle beam mass spectrometer (PBMS) and a function of a scanning electron microscope (SEM).

However, despite the conventional technology including the related art, in the particle beam mass spectrometer according to the conventional technology, detection is performed only when charged particles are cations. Therefore, it is impossible to obtain information in a case where charged particles are anions. In addition, there is a drawback in that only a mass/charge ratio (M/Z) value of a particular range at a particular time can be measured.

Therefore, there is a need for development of a particle beam mass spectrometer that has a new structure, whereby cations and anions can be separated according to the choice of a user and simultaneous measurement of the cations and anions can be performed, and that can measure a total amount of all ions, thereby providing a user with various pieces of information about the size of the fine particles.

DISCLOSURE

Technical Problem

Accordingly, the present invention has been made keeping in mind the above problems occurring in the related art, and an object of the present invention is to provide a particle beam mass spectrometer that can simultaneously measure cations and anions by separating the cations and anions according to the choice of a user, and can measure a total amount of all charged particles including cations and anions.

In addition, another object of the present invention is to provide a method of separating cations and anions for simultaneous measurement thereof, and of obtaining accurate size information of a particle by composing the two measured values, unlike a method of measuring only information of a particle that is positively or negatively charged in the conventional technology.

Technical Solution

In order to accomplish the above object, the present invention provides a particle beam mass spectrometer including: a particle focusing unit focusing a particle beam induced by gas flow; an electron gun forming a charged particle beam by accelerating thermal electrons to ionize the particle beam focused by the particle focusing unit; a deflector deflecting the charged particle beam according to kinetic energy to charge ratio; and a sensing unit measuring a current induced by the deflected charged particle beam, wherein the deflector includes at least one particle beam separation electrode provided at each of opposite sides with respect to a progress axis of the charged particle beam before being deflected.

As an embodiment, each particle beam separation electrode may have a shape selected from a plate shape, a cylindrical shape, a spherical shape, an elliptical shape, and a bar shape with a cross section having a half-circular shape or a quarter-circular shape.

As an embodiment, each particle beam separation electrode may include at least two separation electrodes provided at each of opposite sides with respect to the progress axis of the charged particle beam before being deflected. In this case, each particle beam separation electrode may include an upper separation electrode and a lower separation electrode, whereby a four-pole (quadrupole) shape is provided, and polarities of the separation electrodes respectively provided at positions diagonally facing each other may be the same.

As an embodiment, each particle beam separation electrode may have a quarter-circular shape when viewed from a cross section, and may have a bar shape in a longitudinal direction.

As an embodiment, a positively charged particle and a negatively charged particle may be separated from each other by a voltage applied to each particle beam separation electrode.

As an embodiment, a DC or a combined signal of the DC with RF may be applied to a separation electrode of the particle beam separation electrode.

As an embodiment, the sensing unit may include Faraday cups ranging in number from 1 to 10, and when there is a plurality of the Faraday cups, the sizes of the Faraday cups may be equal to each other or may be different from each other.

As an embodiment, a voltage applied to the particle beam separation electrode may be a DC voltage having a constant value over time, or a signal of one of patterns where a voltage increases or decreases, or the voltage decreases after increases, or the voltage increases after decreases within a particular range over time may be applied to the particle beam separation electrode.

As an embodiment, the particle focusing unit may be provided with an opening positioned at a body of the unit so as to discharge gas to outside.

As an embodiment, at least two openings may be provided in a focus direction of the particle beam.

Advantageous Effects

According to the present invention, the particle beam mass spectrometer can measure cations and anions by separating the cations and anions according to the choice of a user, and can simultaneously measure a total amount of all charged particles including the cations and anions, whereby it is possible to provide various pieces of information to the user, unlike the conventional particle beam mass spectrometer providing only fragmentary information of a particular mass-to-charge ratio value.

Particularly, unlike the conventional method of measuring only information of a particle that is positively or negatively charged such as a cation or an anion, it is possible to provide accurate size information of a particle by separating cations and anions to simultaneously measure the cations and anions, and calculating the sizes of particles according to a predetermined combination.

<Description of the Reference Numerals in the Drawings>

101: particle focusing unit (aerodynamic lens)
102: nozzle
200: turbo molecular pump          201: vacuum chamber
203: skimmer
300: electron gun                  301: filament
302: anode                         304: repeller
400: deflector
500: Faraday cup                   501: electrometer
600: particle beam                 601: charged particle beam
701, 702: particle separation electrode
801~803: Faraday cup

BEST MODE

Hereinafter, an apparatus and method of the present invention will be described in detail with reference to the accompanying drawings. The present invention may be modified in various ways and implemented by various embodiments, so that specific embodiments are shown in the drawings and will be described in detail. However, it should be understood that the present invention is not limited to the specific exemplary embodiments, but includes all modifications, equivalents, and substitutions included in the spirit and the scope of the present invention. In the accompanying drawings, the dimensions of the structures may be enlarged than the actual dimensions for clarity of the invention.

Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 1:
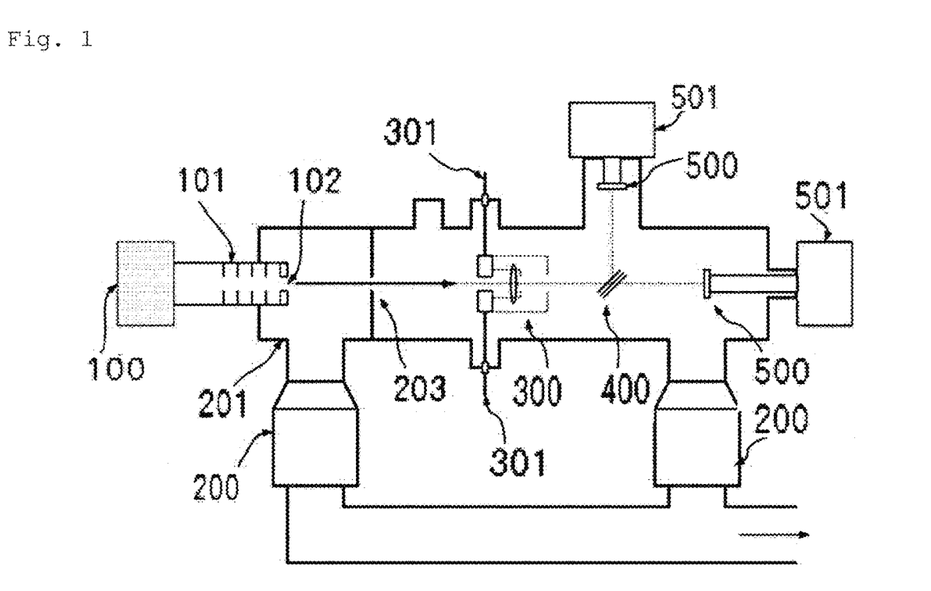
FIG. 1 is a view showing a general particle beam mass spectrometer.

FIG. 1 is a view showing a general particle beam mass spectrometer according to a conventional technology. Specifically, the particle beam mass spectrometer includes: a particle focusing unit 101 focusing a particle beam induced by gas flow; an electron gun 300 forming a charged particle beam by accelerating thermal electrons to ionize the particle beam focused by the particle focusing unit; a deflector 400 deflecting the charged particle beam according to kinetic energy to charge ratio; and a sensing unit 501 measuring a current induced by the deflected charged particle beam.

The particle focusing unit 101 is provided to accelerate particles of an analysis target in the form of beams, and is composed of an aerodynamic lens without being limited thereto, and any configuration capable of simultaneously focusing gas and particles may be used.

Due to the gas flow of the analysis target by the particle focusing unit 101, when aerosols (mixture of gas and particles of the analysis target that are simultaneously introduced) are introduced through the entrance of the particle focusing unit, the aerosols are focused along an axis.

In this case, the particle focusing unit may include a plurality of lenses. Gas and particles of the analysis target that are simultaneously introduced are mixed, and pass through the plurality of lenses in several stages, whereby the particles of the analysis target are focused along the axis of the particle focusing unit.

In this case, the gas, which is introduced together, is relatively lighter than the analysis target particle, and thus the gas may be easily discharged by a vacuum pump of the particle beam mass spectrometer.

The vacuum pump used in the particle beam mass spectrometer of the present invention may be a pump that maintains a vacuum region having a range equal to or less than $10^{-2}$ mbar, and preferably, may be a vacuum pump that maintains a vacuum region having a range equal to or less than $10^{-5}$ mbar, or a range equal to or less than $10^{-6}$ mbar as a relatively higher vacuum range.

For example, the vacuum chamber may include a dry pump, a diffusion pump, a turbo molecular pump, an ion pump, a cryopump, a rotary pump, and at least one selected from dry pumps such as a scroll or diaphragm pump, etc. or a combination thereof.

That is, the gas and the analysis target particles that are introduced through the particle focusing unit are accelerated through a nozzle 102 of the final lens in the particle focusing unit 101. At a region where the gas and the analysis target particles may be collided with electrons generated by the electron gun, the gas and the analysis target particles collide with the electrons, and thus charged particles are formed and flow toward the deflector.

In addition, it is required to maintain the particle beam mass spectrometer of the present invention in a high vacuum state. To this end, the components may be used as being provided in a vacuum chamber or including the vacuum chamber.

Figure 2:
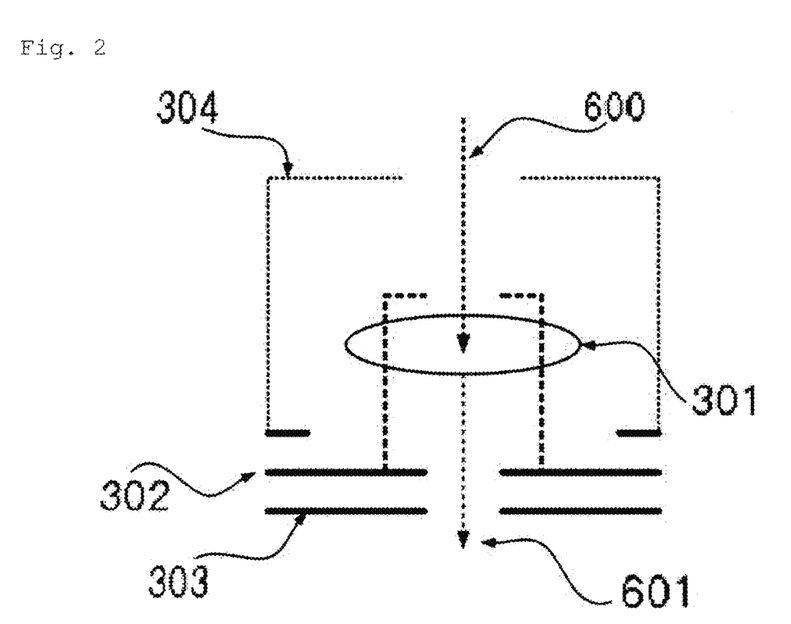
FIG. 2 is a view showing an example of an electron gun in the particle beam mass spectrometer of FIG. 1.

FIG. 2 is a view showing an example of the electron gun in the particle beam mass spectrometer of FIG. 1.

As shown in FIG. 2, the electron gun 300 accelerates thermal electrons by using a filament to ionize the particle beam focused by the particle focusing unit. The electron gun includes: an anode 302 which is a positive electrode; a repeller 304 having a cylindrical shape and provided outside of the anode 302; and a filament 301 provided between the anode 302 and the repeller 304, the filament generating the thermal electrons.

In this case, in order to generates a restriction magnetic field ($B_z$) restricting the thermal electrons, a magnetic field generating unit provided outside of an external net may be included.

The electron gun 300 charges the gas including particles introduced through the nozzle, until the gas is saturated.

To this end, electrons generated by the filament collide with the particle beam in the electron gun, whereby secondary electrons are discharged, and charged particles are formed.

In the meantime, the deflector may be referred to as an electrostatic deflector in the present invention. The deflector defects the charged particle beam according to kinetic energy to charge ratio, whereby the sizes of particles are classified by using a charge ratio difference for each particle size. The deflector outputs only particles having a particular size towards a detector by applying a particular voltage as a load.

Figure 3:
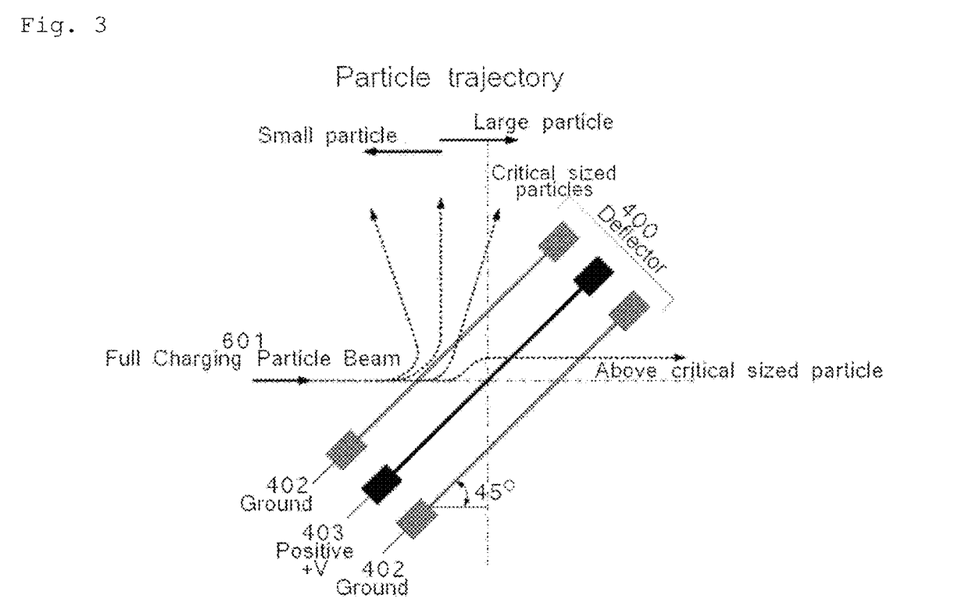
FIG. 3 is a view showing a particle filter in the particle beam mass spectrometer of FIG. 1.

FIG. 3 is a view showing an example of the deflector according to the conventional technology. Shown is a defector of the particle beam mass spectrometer in FIG. 1. The defector according to the conventional technology as shown in FIG. 3 is composed of plates that are three sheets of mesh. An electric field is generated by applying a positive (+) voltage to a mesh plate 403 provided at the middle of the mesh, and plates 402 provided at opposite side of the middle plate are grounds.

Here, there is a relation between a particle having a particular size and a particular voltage. Accordingly, in a case of a positively charged particle, a charged particle beam 601 toward the center of the deflector is deflected by the positive voltage applied to the middle plate. A particle that is lighter than a critical sized particle is deflected at an acute angle, less than a 90-degree angle, with respect to an incidence angle of a charged particle, and a particle that is heavier than the critical sized particle may be deflected at an obtuse angle, larger than a 90-degree angle.

For example, when a voltage of 1,000 V is applied and a particle having a size of 200 nm is a critical sized particle, the route of the particle may be changed at a 90-degree angle and the particle may be provided to a Faraday cup.

In the meantime, the sensing unit measures a current induced by the deflected charged particle beam, and generally, a Faraday cup is used as the sensing unit.

The Faraday cup is a simple metal board having a rear surface connected to an electrode. When particles latch onto a Faraday cup, positive ions of the particles are provided to the electrode and a current value of the electrode is measured by using a measuring instrument, whereby a current induced by the charged particle beam is measured.

According to the above-described configurations of the particle beam mass spectrometer based on the conventional technology, concentration of collected particles may be indirectly assumed by measuring a current amount of a counter. However, detection is performed only when charged particles are cations. Therefore, it is impossible to obtain information in a case where charged particles are anions. In addition, there is a drawback in that only a mass/charge ratio (M/Z) value of a particular range at a particular time can be measured.

Unlike a method of calculating a size of a particle by measuring a current level of only one of a cation and an anion, in the present invention, based on that the charged particle may exist as a cation and an anion, current levels of both a cation and an anion are measured, whereby information such as a size of a particle, etc. can be specifically calculated by using relatively many pieces of information, and a particle beam mass spectrometer realizing the method can be provided.

That is, when the charged particle collides with a particle emitted from the electron gun, the charged particle may be in a positive (+) state or a negative (−) state.

For example, in order to obtain information of a silicon nitride ($Si_3N_4$) particle in a deposition process or a cleaning process of semiconductor process, cation measurement and anion measurement may be performed under respective conditions.

As a more specific exemplary condition, in the electron gun, 160 V is applied to the anode 302, 60 V is applied to the filament 301, 70 V is applied to a focus lens 303. When measuring cations, 1,200 V is applied to the deflector 400 according to the conventional technology, and when measuring anions, −1,200V is applied to the deflector 400 according to the conventional technology. When performing deposition process, pressure is 4.5 Torr, and when performing cleaning process, pressure is 5.5 Torr. When a base pressure of the particle beam mass spectrometer is low $10^{-6}$ Torr, information of each of the cations and anions may be obtained.

Accordingly, the particle beam mass spectrometer of the present invention includes: the particle focusing unit 101; the electron gun 300; the deflector 400; and the sensing unit 501. The deflector includes at least one particle beam separation electrode provided at each of opposite sides with respect to a progress axis of the charged particle beam before being deflected.

Figure 4:
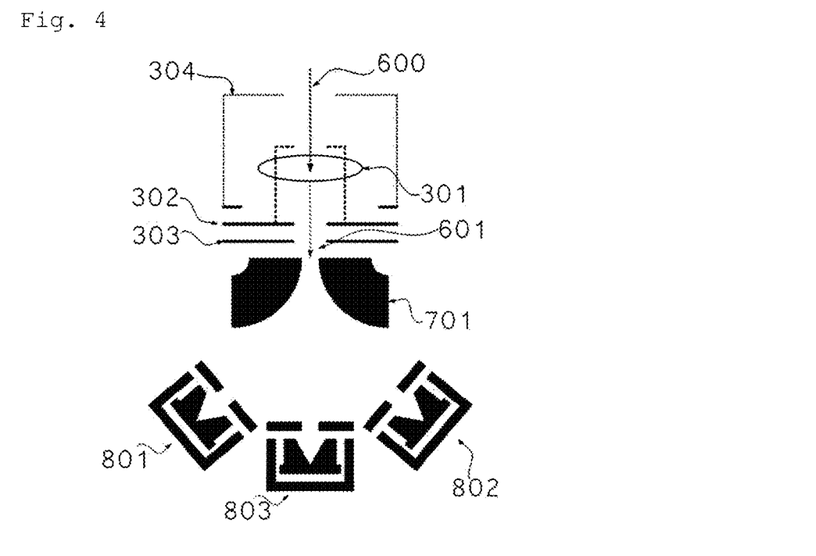
FIG. 4 is a view showing configurations of a dipole particle beam separation electrode and Faraday cups of a particle beam mass spectrometer according to an embodiment of the present invention.

This will be disclosed in detail with reference to FIG. 4.

FIG. 4 is a view showing configurations of a dipole particle beam separation electrode and Faraday cups of a particle beam mass spectrometer according to an embodiment of the present invention.

Referring to FIG. 4, the deflector of the present invention includes a dipole particle beam separation electrode as providing one separation electrode at each of opposite sides with respect to an axis in a progression direction of the charged particle beam formed by the electron gun.

In addition, in FIG. 4, as the sensing unit measuring a current induced by the charged particle beam, three Faraday cups are provided at a left side portion, a middle portion, and a right side portion below the dipole particle beam separation electrode (separator).

Here, when polarities of voltages of the dipole particle beam separation electrode are different from each other, a positively charged particle and a negatively charged particle have moving paths different from each other. In addition, each trajectory may be dependent on the range of a voltage of the dipole particle beam separation electrode.

That is, the deflector in the particle beam mass spectrometer of the present invention may adjust a moving direction and a trajectory of a charged particle generated by the electron gun depending on a polarity of and a size of a voltage applied to each particle beam separation electrode. Accordingly, unlike the conventional method of measuring only information of a particle that is positively or negatively charged such as a cation or an anion, accurate size information of a particle may be provided by separating cations and anions to simultaneously measure the cations and anions, and calculating the sizes of particles according to a predetermined combination.

Figure 5:
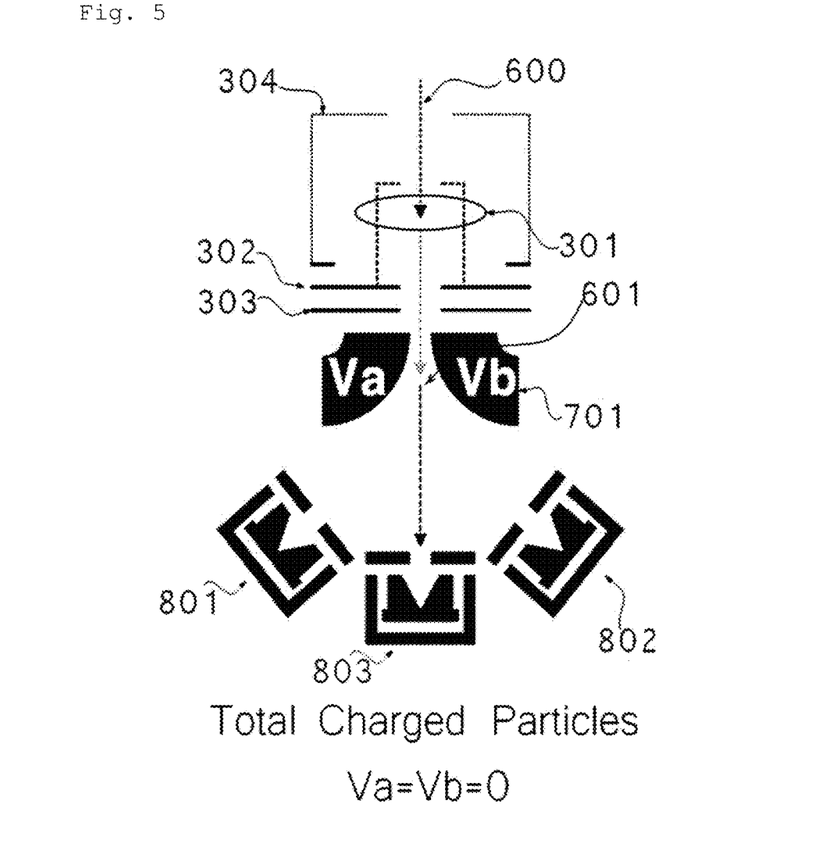
FIG. 5 is a view showing a process of collecting a total charged particle beam in operation of a dipole particle beam separation electrode of a particle beam mass spectrometer according to an embodiment of the present invention.
Figure 6:
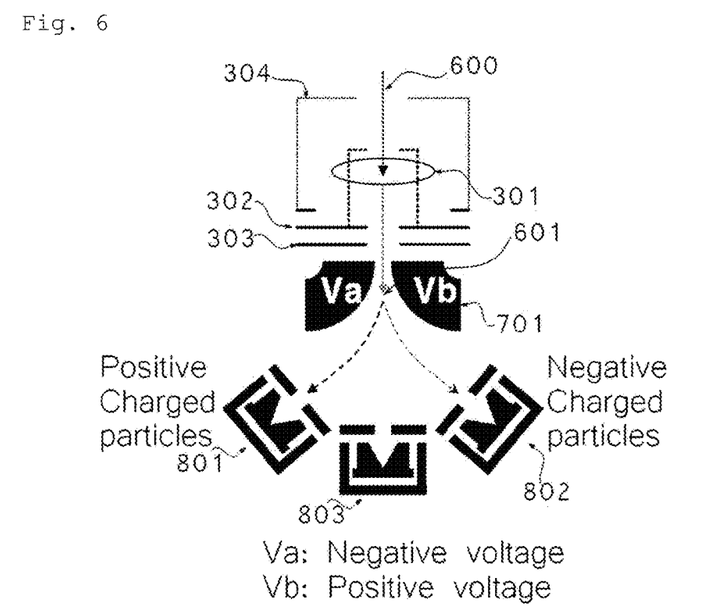
FIG. 6 is a view showing a process of separating a cation and an anion, and simultaneously collecting the cation and the anion at different Faraday cups in operation of a dipole particle beam separation electrode of a particle beam mass spectrometer according to an embodiment of the present invention.

This will be disclosed in detail with reference to FIGS. 5 and 6.

FIG. 5 is a view showing a process of collecting a total charged particle beam in operation of a dipole particle beam separation electrode of a particle beam mass spectrometer according to an embodiment of the present invention.

As described in FIGS. 1 and 2, in the particle beam mass spectrometer (PBMS) equipped with the deflector of FIG. 4, through an aerodynamic lens, etc. as a particle focusing unit, analysis target particles are gathered at the middle part of the aerodynamic lens due to gas flow, and are accelerated due to expansion from the nozzle. The particle beam of the analysis target is incident to a region of the electron gun 300 by having sufficient inertia moment. The electron gun 300 emits thermal electrons by using the filament 301, and the emitted thermal electrons are accelerated to ionize the particle beam, whereby a charged particle beam is formed. As a deflector, the charged particle beam is classified by a dipole particle beam separation electrode 701 according to kinetic energy to charge ratio. In this case, in FIG. 5, a special voltage is not applied to respective electrodes of the dipole particle beam separation electrode ($V_a$=$V_b$=0), and thus a positively charged particle and a negatively charged particle are incident to a Faraday cup positioned at the middle portion, whereby currents thereof may be measured and all charged particles may be collected.

In addition, the positively charged particle and the negatively charged particle may be separated from each other by respective voltages applied to the particle beam separation electrode of the deflector in the present invention. This will be disclosed with reference to FIG. 6.

FIG. 6 is a view showing a process of separating a cation and an anion, and simultaneously collecting the cation and the anion at different Faraday cups in operation of a dipole particle beam separation electrode of a particle beam mass spectrometer according to an embodiment of the present invention.

As shown in FIG. 6, in the particle beam charged by the electron gun, respective voltages ($V_a$ and $V_b$) applied to the dipole particle beam separation electrode 701 have opposite polarities, and a positively charged particle and negatively charged particle may be separated and simultaneously collected.

For example, when the Va is a negative voltage and the Vb is a positive voltage, positively charged particles may be collected at Faraday cup of the left side and negatively charged particles may be collected at Faraday cup of the right side.

In the meantime, at the particle beam separation electrode of the present invention, a DC (direct current voltage) as well as RF, and a combined signal of the DC and the RF may be applied to the separation electrode.

In this case, preferably, a voltage applied to the particle beam separation electrode is a DC voltage having a constant value over time. Alternatively, a signal of one of patterns where the voltage increases or decreases, or the voltage decreases after increases, or the voltage increases after decreases within a particular range over time is applied to the particle beam separation electrode.

In addition, each particle beam separation electrode, which is a component of the deflector of the present invention, may have a shape selected from a plate shape, a cylindrical shape, a spherical shape, an elliptical shape, and a bar shape with a cross section having a half-circular shape or a quarter-circular shape, but it is possible to use any shape as a conductor capable of applying a voltage in a range that may change the moving path of the charged particle beam without being limited to the types.

In addition, the sensing unit of the present invention includes Faraday cups ranging in number from 1 to 10. When there is a plurality of the Faraday cups, the sizes of the Faraday cups may be equal to each other or are different from each other.

In addition, each particle beam separation electrode of the present invention may include at least two separation electrodes provided at each of opposite sides with respect to the progress axis of the charged particle beam before being deflected.

In this case, each particle beam separation electrode has an upper separation electrode and a lower separation electrode whereby a four-pole (quadrupole) shape is provided, and polarities of the separation electrodes respectively provided at position diagonally facing each other are the same.

More specifically, each particle beam separation electrode has a quarter-circular shape when viewed from a cross section, and has a bar shape in a longitudinal direction.

The particle beam mass spectrometer having such configuration will be disclosed in detail with reference to FIGS. 7 to 10.

Figure 7:
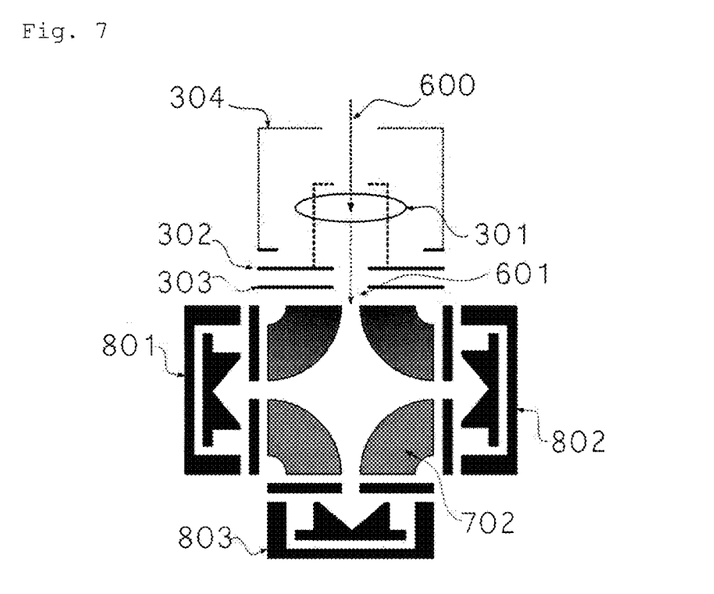
FIG. 7 is a view showing configurations of a quadrupole particle beam separation electrode and Faraday cups of a particle beam mass spectrometer according to an embodiment of the present invention.

FIG. 7 is a view showing configurations of a quadrupole particle beam separation electrode and Faraday cups of a particle beam mass spectrometer according to an embodiment of the present invention.

As shown in FIG. 7, the deflector of the present invention includes each particle beam separation electrode 702 having an upper separation electrode and a lower separation electrode provided at each of opposite sides with respect to a progress axis of the charged particle beam before being deflected by the deflector, whereby a quadrupole particle beam separation electrode is configured to have a four-pole (quadrupole) shape.

In addition, in FIG. 7, as the sensing unit measuring a current induced by the charged particle beam, three Faraday cups are provided at a left side portion 801, a middle portion 803, and a right side portion 802 below the quadrupole particle beam separation electrode 702.

Figure 8:
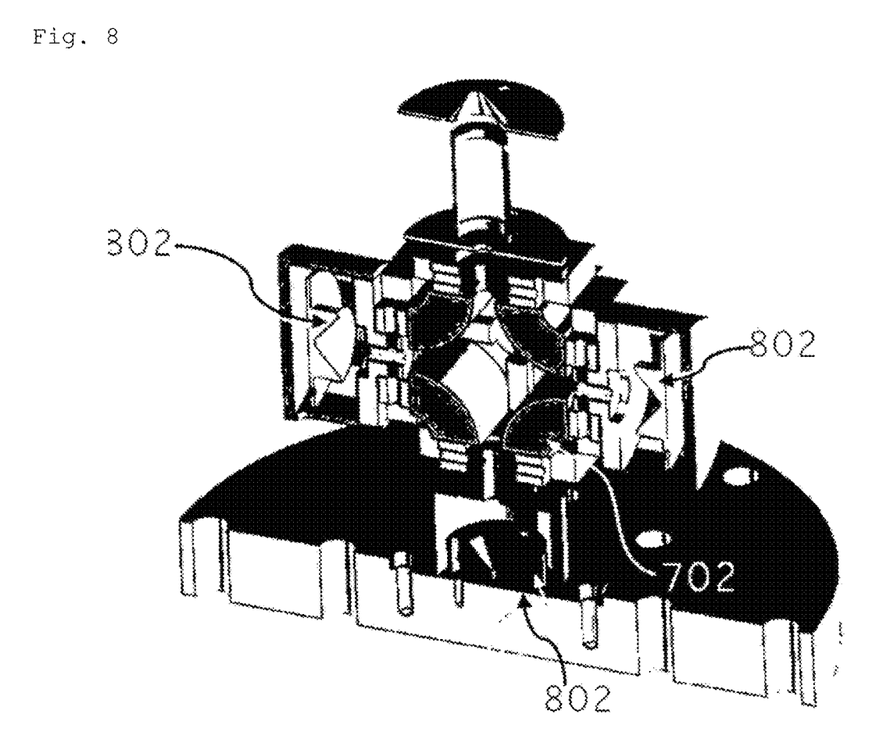
FIG. 8 is a view showing three-dimensional configurations of an electron gun, a quadrupole particle beam separation electrode, and Faraday cups of a particle beam mass spectrometer according to an embodiment of the present invention.

FIG. 8 is a view showing three-dimensional configurations of an electron gun, a quadrupole particle beam separation electrode 702, and Faraday cups of a particle beam mass spectrometer according to FIG. 7.

Referring to FIG. 8, each quadrupole particle beam separation electrode 702 of FIG. 7 has a quarter-circular shape when viewed from a cross section, and has a bar shape in a longitudinal direction. In addition, the inner space of the quadrupole particle beam separation electrode may be an empty space depending on needs selectively.

Polarities and ranges of respective voltages of the quadrupole particle beam separation electrode of FIG. 7 are adjusted, whereby moving paths of a positively charged particle and a negatively charged particle are changed as shown in FIGS. and 6, and each trajectory may be adjusted. Accordingly, unlike the conventional method of measuring only information of a particle that is positively or negatively charged such as a cation or an anion, accurate size information of a particle may be provided by separating cations and anions to simultaneously measure the cations and anions, and calculating the sizes of particles according to a predetermined combination.

Figure 9:
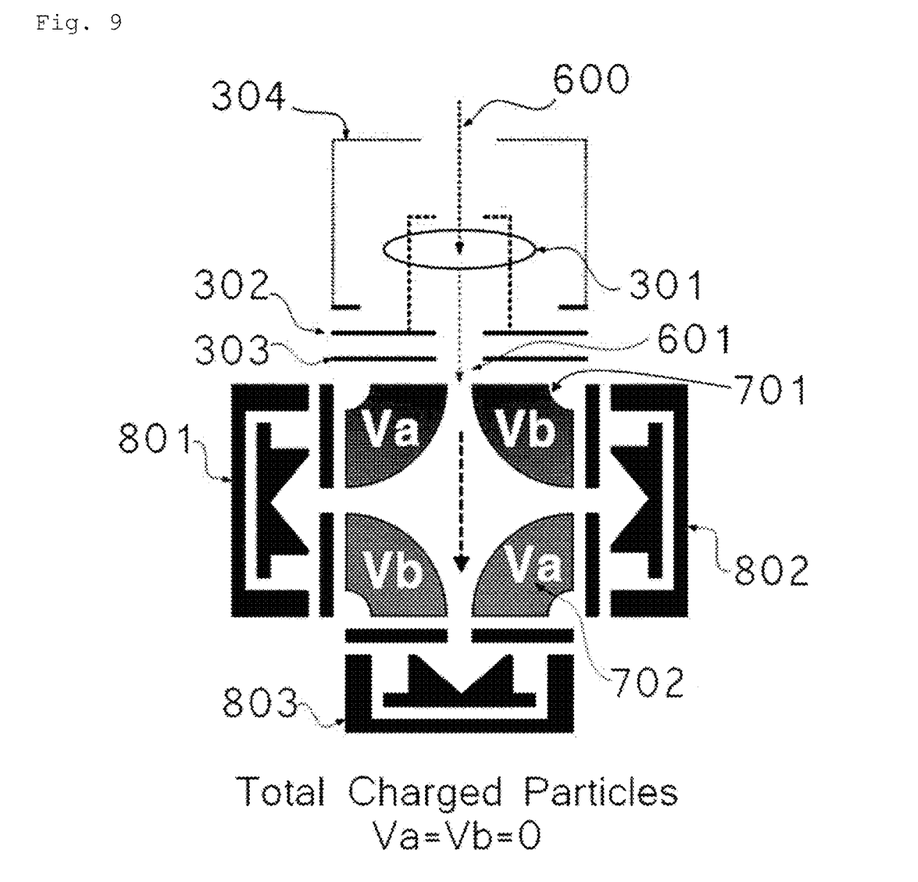
FIG. 9 is a view showing a process of collecting all charged particles in operation of a quadrupole particle beam separation electrode of a particle beam mass spectrometer according to an embodiment of the present invention.

FIG. 9 is a view showing a process of collecting all charged particles generated by the quadrupole particle beam separation electrode.

As shown in FIG. 5, the charged particle beam that is formed at the particle beam mass spectrometer having the deflector of FIG. 7 is classified by the quadrupole particle beam separation electrode 702 according to kinetic energy to charge ratio. In this case, in FIG. 9, a special voltage is not applied to respective electrodes of the quadrupole particle beam separation electrode ($V_a = V_b = 0$), and thus a positively charged particle and a negatively charged particle are incident to a Faraday cup 803 positioned at the middle portion, whereby current values thereof may be measured and all charged particles may be collected.

Figure 10:
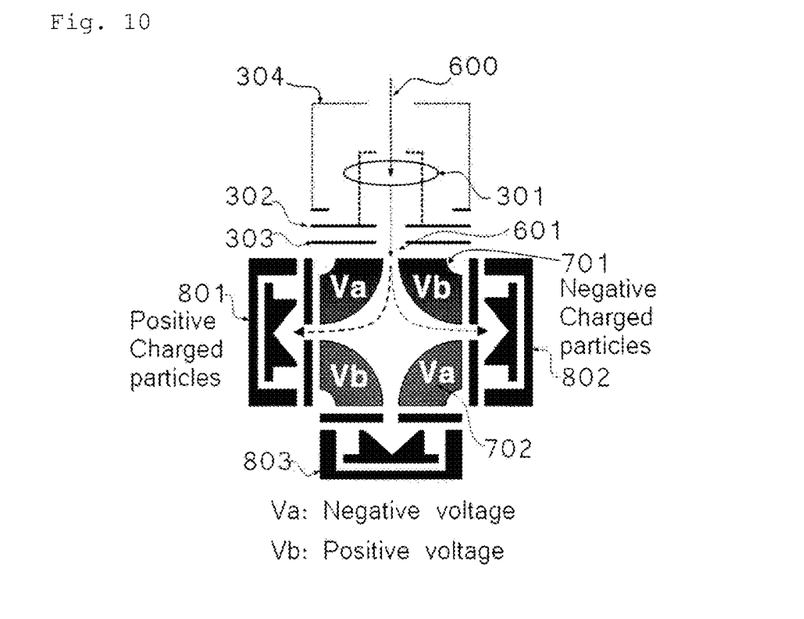
FIG. 10 is a view showing a process of separating a cation and an anion, and simultaneously collecting the cation and the anion at different Faraday cups in operation of a quadrupole particle beam separation electrode of a particle beam mass spectrometer according to an embodiment of the present invention.

In addition, in FIG. 10, voltages applied to respective particle beam separation electrodes of the quadrupole particle beam separation electrode are adjusted, whereby a positively charged particle and a negatively charged particle may be separated from each other.

FIG. 10 is a view showing a process of separating a cation and an anion, and simultaneously collecting the cation and the anion at different Faraday cups in operation of a quadrupole particle beam separation electrode of a particle beam mass spectrometer according to an embodiment of the present invention.

As shown in FIG. 10, in the particle beam charged by the electron gun, when voltages applied to particle beam separation electrodes diagonally facing each other (each $V_a$, or each $V_b$) are the same, and polarities of adjacent separation electrodes (for example, $V_a$ of 702 and $V_b$ of 701) are opposite to each other, the positively charged particle and the negatively charged particle may be collected by being separated.

For example, when the Va is a negative voltage and the Vb is a positive voltage, positively charged particles may be collected at Faraday cup of the left side and negatively charged particles may be collected at Faraday cup of the right side.

Figure 11:
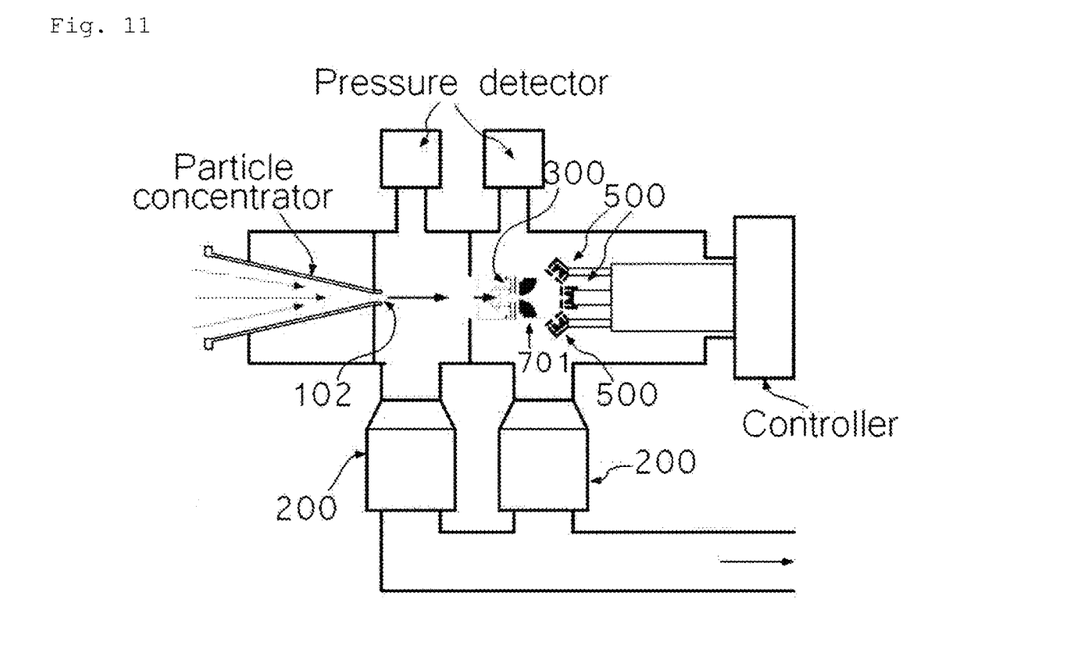
FIG. 11 is a view showing a particle beam mass spectrometer equipped with a dipole particle beam separation electrode according to an embodiment of the present invention.
Figure 12:
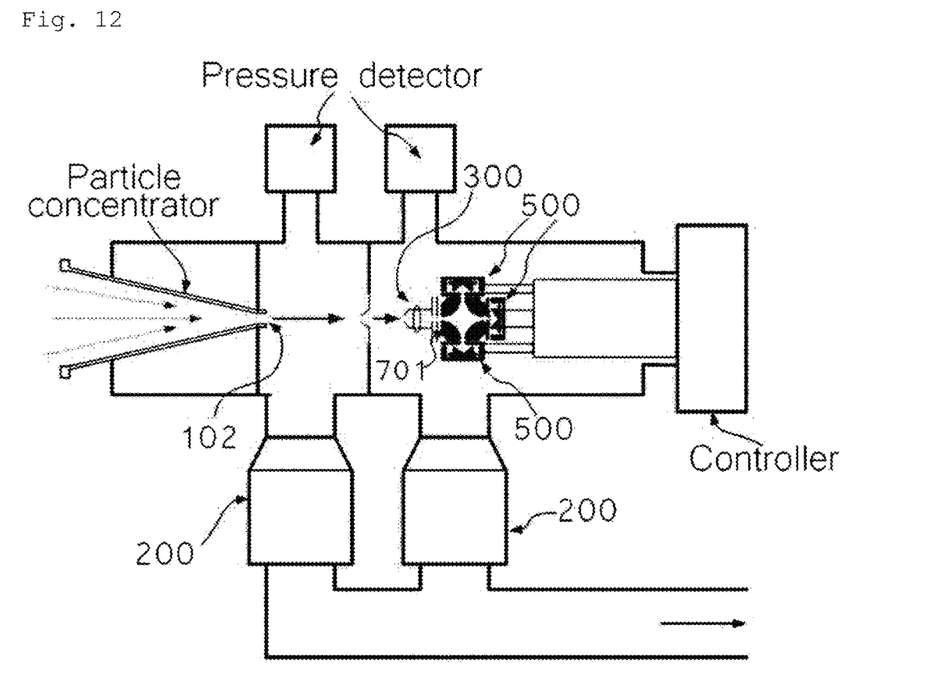
FIG. 12 is a view showing a particle beam mass spectrometer equipped with a quadrupole particle beam separation electrode according to an embodiment of the present invention.

FIGS. 11 and 12 show configurations of the particle beam mass spectrometer according to the present invention. Specifically, FIG. 11 is a view showing that a dipole particle beam separation electrode is provided as a deflector in a particle beam mass spectrometer according to an embodiment of the present invention.

In the meantime, the particle focusing unit of the present invention may be provided with an opening positioned at a body of the unit so as to discharge gas to outside. Preferably, at least two openings may be provided in a focus direction of the particle beam, and more preferably, at least three openings, more preferably, at least four openings may be provided.

With such structure, particles having kinetic energy relatively larger than gas are focused to the center by the focusing unit, and the light gas is discharged through the opening due to the pressure difference between inside and outside of the focusing unit. As described above, sample gas is progressed by the focusing unit, and thus particles are gradually accumulated at the center. The particles having passed through the nozzle 102 are finally separated from gas, and are charged by being introduced into a skimmer 203 orifice having a diameter of 2-3 mm.

As shown in FIG. 11, in the particle beam mass spectrometer, the analysis target particles are introduced by gas flow from a final nozzle 102 at the particle focusing unit focusing the particle beam into the electron gun 300 to form charged particles. The formed charged particle beam may be adjusted by the deflector 701 by being deflected, or may go straight and may be collected at Faraday cup 500 without being deflected.

In addition, FIG. 12 is a view showing that a quadrupole particle beam separation electrode is provided as a deflector in a particle beam mass spectrometer according to an embodiment of the present invention.

As shown in FIG. 11, the charged particle beam formed by the electron gun 300 may be adjusted by the deflector 701 by being deflected, or may go straight and may be collected at Faraday cup 500 without being deflected.

Accordingly, as described above, the particle beam mass spectrometer of the present invention can simultaneously measure cations and anions by separating the cations and anions according to the choice of a user, or can separate cations and anions and simultaneously measure the cations and anions, whereby a total amount of all charged particles including the cations and anions. Accordingly, it is possible to provide various pieces of information to the user, unlike the conventional particle beam mass spectrometer providing only fragmentary information of a particular mass-to-charge ratio value.

In addition, levels of the cation and the anion are separated and measured, and two signals thereof are composed, whereby measurement data of a target particle signal is strengthened. Such strengthening of the measurement data increases reliability of the calculation result of the target particles.

Although the configurations of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

According to the present invention, a particle beam mass spectrometer can simultaneously measure cations and anions by separating the cations and anions according to the choice of a user in the analysis, etc. of fine particles generated during semiconductor process, and thus the particle beam mass spectrometer is industrially applicable.

The invention claimed is:

1. A particle beam mass spectrometer comprising:
a particle focusing unit focusing a particle beam induced by gas flow;
an electron gun forming a charged particle beam including a positive ion or a negative ion by accelerating thermal electrons to ionize the particle beam focused by the particle focusing unit;
a deflector deflecting the charged particle beam according to kinetic energy to charge ratio; and
a sensing unit measuring a current induced by the deflected charged particle beam,
wherein the deflector includes at least one particle beam separation electrode provided at each of opposite sides with respect to a progress axis of the charged particle beam before being deflected, and
the sensing unit is configured to simultaneously collect the positive ion and the negative ion in different regions of the sensing unit, wherein the positive ion and the negative ion are separated from each other by a voltage applied to the at least one particle beam separation electrode.

2. The particle beam mass spectrometer of claim 1, wherein each particle beam separation electrode has a shape selected from a plate shape, a cylindrical shape, a spherical shape, an elliptical shape, and a bar shape with a cross section having a half-circular shape or a quarter-circular shape.

3. The particle beam mass spectrometer of claim 1, wherein each particle beam separation electrode includes at least two separation electrodes provided at each of opposite sides with respect to the progress axis of the charged particle beam before being deflected.

4. The particle beam mass spectrometer of claim 3, wherein each particle beam separation electrode includes an upper separation electrode and a lower separation electrode, whereby a four-pole (quadrupole) shape is provided, and polarities of the separation electrodes respectively provided at positions diagonally facing each other are same.

5. The particle beam mass spectrometer of claim 4, wherein each particle beam separation electrode has a quarter-circular shape when viewed from a cross section, and has a bar shape in a longitudinal direction.

6. The particle beam mass spectrometer of claim 1, wherein a DC or a combined signal of the DC with RF is applied to a separation electrode of the particle beam separation electrode.

7. The particle beam mass spectrometer of claim 6, wherein a voltage applied to the particle beam separation electrode is a DC voltage having a constant value over time, or a signal of one of patterns where a voltage increases or decreases, or the voltage decreases after increases, or the voltage increases after decreases within a particular range over time is applied to the particle beam separation electrode.

8. The particle beam mass spectrometer of claim 1, wherein the sensing unit includes Faraday cups ranging in number from 1 to 10, and when there is a plurality of the Faraday cups, the sizes of the Faraday cups are equal to each other or are different from each other.

9. The particle beam mass spectrometer of claim 1, wherein the particle focusing unit is provided with an opening positioned at a body of the unit so as to discharge gas to outside.

10. A method of obtaining information about a size or a density or both of a particle by using the particle beam mass spectrometer of claim 1.

* * * * *